United States Patent
Kitaoka et al.

(10) Patent No.: US 6,174,326 B1
(45) Date of Patent: Jan. 16, 2001

(54) RADIOPAQUE, ANTITHROMBOGENIC STENT AND METHOD FOR ITS PRODUCTION

(75) Inventors: Takashi Kitaoka; Kazuhiko Hagiwara; Yousuke Moriuchi, all of Shizuoka (JP)

(73) Assignee: Terumo Kabushiki Kaisha, Tokyo (JP)

( * ) Notice: Under 35 U.S.C. 154(b), the term of this patent shall be extended for 0 days.

(21) Appl. No.: 08/935,686

(22) Filed: Sep. 23, 1997

(30) Foreign Application Priority Data

Sep. 25, 1996 (JP) .................................................. 8-252852

(51) Int. Cl.⁷ ................................. A61F 2/06; A61L 27/16
(52) U.S. Cl. ........................... 623/1; 623/1.46; 623/1.34; 606/194
(58) Field of Search ................... 623/1, 12, 11; 606/191, 195, 194, 198

(56) References Cited

U.S. PATENT DOCUMENTS

| | | | |
|---|---|---|---|
| 3,810,781 | 5/1974 | Eriksson et al. | 117/47 A |
| 4,118,485 | 10/1978 | Eriksson et al. | 424/183 |
| 4,733,665 | 3/1988 | Palmaz | 128/343 |
| 4,739,762 | 4/1988 | Palmaz | 128/343 |
| 4,776,337 | 10/1988 | Palmaz | 128/343 |
| 5,104,404 | 4/1992 | Wolff . | |
| 5,201,901 | 4/1993 | Harada et al. . | |
| 5,356,433 * | 10/1994 | Rowland et al. | 623/1 |
| 5,383,928 * | 1/1995 | Scott et al. | 623/1 |
| 5,593,434 | 1/1997 | Williams . | |
| 5,607,442 * | 3/1997 | Fischell et al. | 623/1 |
| 5,725,572 * | 3/1998 | Lam et al. | 623/1 |
| 5,876,433 | 3/1999 | Lunn . | |

FOREIGN PATENT DOCUMENTS

| | | |
|---|---|---|
| 0 351 314 | 1/1990 | (EP) . |
| 0679372 | 11/1995 | (EP) . |
| 0679373 | 11/1995 | (EP) . |
| 756853 | 2/1997 | (EP) . |
| 824900 | 2/1998 | (EP) . |
| 873732 | 10/1998 | (EP) . |
| B-5-43392 | 7/1993 | (JP) . |
| 6-105902 | 4/1994 | (JP) . |
| B-6-38851 | 5/1994 | (JP) . |

* cited by examiner

Primary Examiner—Paul B. Prebilic
Assistant Examiner—Choon P. Koh
(74) Attorney, Agent, or Firm—Burns, Doane, Swecker & Mathis, LLP

(57) ABSTRACT

A stent having long-term antithrombogenicity and radiopacity whose location and geometry can be radiographically confirmed is provided. The production method is also provided. The stent of the invention has an antithrombogenic agent covalently bonded on it surface, and the antithrombogenic agent is immobilized onto the stent surface through coupling agent having at least two amino groups and a crosslinking agent having at least two aldehyde and/or epoxy groups. The stent of the invention also has a radiopaque metal plated on at least a part thereof.

10 Claims, 4 Drawing Sheets

RADIOPAQUE, ANTITHROMBOGENIC STENT AND METHOD FOR ITS PRODUCTION

BACKGROUND OF THE INVENTION

This invention relates to a stent used for dilating a stenotic lesion of a blood vessel.

PTCA (percutaneous transluminal coronary angioplasty) is a widely adopted treatment in the case of coronary artery stenotic diseases such as stenocardia and myocardial infarction. In PTCA, the stenotic lesion of the blood vessel (coronary artery) is pushed open from its inside to enable the blood to flow therethrough.

In order to avoid restenosis of the blood vessel after the blood vessel dilatation, an expandable intraluminal graft ("stent") as disclosed in U.S. Pat. No. 4,733,665 has been developed.

A stent is a cylindrical medical device used to maintain the inside opening of a body duct such as a blood vessel and bile duct. The stent is introduced into the body duct in compacted or folded thin state. When the stent is positioned in the target site (stenosis lesion), the stent is expanded and pressed into place against the inner wall of the lumen and stands there to serve a structural support for the lumen.

There are two mechanisms for the stent expansion. One is the mechanism wherein the stent is pushed radial-outwardly from its inside by a n external force, namely, by placing a balloon inside the stent and inflating the balloon. The other is the mechanism wherein a stent capable of restoring its original shape is folded in a compact shape, and the force retaining such compact shape is removed to allow for the stent to self-expand in radially outward direction by its own restorative force.

The stent of the first type which is expanded in radially outward direction by the external force of the inflated. balloon is called a balloon-expanded stent, and the stent of this type is not self-expandable. The balloon-expanded stent is made of a metal material which is less likely to restore its original shape once the stent is expanded, and in view of biological safety, the preferred materials are inactive in a body such as stainless steel, tantalum, and the like.

The stent that expands by its own restorative force is called a self-expandable stent, and the stent of this type is provided with a constriction means and is selfexpandable. For example, the stent may be constricted and accommodated in a tube having an outer diameter smaller than the inner diameter of the target lesion, and once the distal end of the tube has reached the target lesion, the stent may be pushed out of the tube to allow its self-expansion. As described above, the self-expandable stent should be capable of restoring its original shape, and therefore, such stent is made from stainless steel, a superelastic alloy, or a shape memory alloy (nickel-titanium alloy, in the latter two cases).

Of the self-expandable stents, the one employing a superelastic alloy (shape memory alloy) is disclosed in JP-B-5-43392.

As described above, most of currently available stents are made of a metal. A metal has been selected in view of its inherent physical properties and particular function as well as safety and compatibility with the tissue. A metal, however, is an utterly foreign matter from the standpoint of blood, and the blood induces thrombus formation and platelet activation to induce vascular smooth muscle cell (VSMC) migration and proliferation.

Since the stent generally has a complex net structure, the placement is always involved with some risk of narrowing or blockage of the blood vessel by thrombus formation or vascular smooth muscle cell migration and proliferation, and this is the reason why the patient is administered with an antithrombotic agent such as heparin or warfarin for approximately two weeks following the stent placement until the inner surface of the stent is substantially covered with hemangioendothelial cells. Such administration of the antithrombotic agent may result in the occurrence of a bleeding complication from the artery at the puncture site or from the peripherals.

If the restenosis short after the stent placement induced by the vascular smooth muscle cell migration and proliferation through the platelet activation could be avoided, and dosage and period of the antithrombotic administration could be reduced or nulled, the results should be shorter lengths of hospital stay and decreased bleeding complications.

In the meanwhile, various methods have been developed for the purpose of rendering medical devices antithrombogenic.

U.S. Pat. No. 3,810,781 discloses a method for imparting antithrombogenicity with a surface of plastic resin wherein a cationic surfactant is adsorbed on the plastic surface, and heparin which has been crosslinked with glutaraldehyde is ionically bonded to the surfactant.

U.S. Pat. No. 4,118,485 discloses a method for imparting antithrombogenicity with a surface of substrate of a plastic resin, glass, or metal wherein the substrate surface is coated with a heparin-quaternary amine complex compound, and the surface is further treated with glutaraldehyde to form a Schiff base to thereby impart antithrombogenicity with the substrate surface. There is also disclosed a method wherein the substrate surface is coated with a heparin-quaternary amine (benzalkonium chloride) complex compound to impart antithrornbogenicity with the substrate surface.

In these methods, however, the heparin, the heparin-quaternary amine compound, or the heparin-quaternary amine-glutaraldehyde compound is attached to the substrate surface through IPN (interpenetrating network) structure or intermolecular force, and therefore, the heparin-substrate bond is not sufficiently strong as in the case of covalent bond.

EP-A-679373 discloses a method wherein the stent is imparted with antithrombogenicity by vacuum depositing a Parylene resin coating on the stent.

JP-B-6-38851 discloses various methods for covalently bonding heparin or a derivative thereof to the surface of various plastic resin materials. In these methods, the heparin derivative is covalently bonded to the substrate surface, and the heparin derivative is unlikely to be removed from the surface. However, in the case of metal material which is less active than the plastic material, it is unknown whether such heparin derivative can be covalently bonde d to the metal surface by the same procedure. Even if such heparin derivative could be covalently bonded to the metal surface of a stent, it is still unknown whether the heparin derivative can effectively suppress the vascular smooth muscle cell migration and proliferation.

Stainless steel, the most widely adopted material for a stent, is radiotranslucent, and since a stent has a net structure, and the width of the stainless steel item which constitutes a net has a thickness of 0.2 mm, it has been quite difficult to confirm the exact location and the geometry of the radiotranslucent stainless steel stent during and after the surgery. A radiopaque marker has been provided on the catheter to indicate the location of the stent. Such radiopaque markers on the catheter, however, have been far from being satisfactory since there is a considerable risk of the stent becoming displaced from the predetermined site on the catheter. In addition, incapability of direct confirmation of the catheter geometry often resulted in the failure of finding the event of insufficient stent expansion and "elastic recoiling" which is the recovery of the once expanded stent to its initial unexpanded state by the restoration tendency to some extent inherent to all metal materials.

In order to obviate such situation, EP-A-679372 discloses a stent provided with a radiopaque marker. A stent plated with a metal for the purpose of imparting radiopacity, however, suffers from the risk of inducing the narrowing and blocking of the b lood vessel at the site where it is placed.

SUMMARY OF THE INVENTION

In view of the above-described situation, an object of the present invention is to provide a stent having a long-term antithrombogenicity as well as excellent tissue reformability.

Another object of the present invention is to provide a stent whose location and geometry can be confirmed by X-ray irradiation.

Another object of the present invention is to provide a method for producing such a stent.

Such objects of the present invention are attained by the present invention summarized in the following (1) to (8). (1) A stent wherein an antithrombogenic agent is covalently bonded to a substrate which has been treated with an oxidizing agent through a coupling agent having at least two amino groups and a crosslinking agent having at least two aldehyde and/or epoxy groups.

(2) A stent according to the above (1) wherein said oxidizing agent is ozone.

(3) A stent according to the above (1) or (2) wherein said antithrombogenic agent is aminated heparin.

(4) A stent according to the above (1) wherein said substrate comprises stainless steel.

(5) A stent according to the above (1) wherein said coupling agent is at least one member selected from the group consisting of polyethylene imine, polyethylene glycol diamine, ethylenediamine, and tetramethylenediamine.

(6) A stent according to the above (1) wherein said crosslinking agent is glutaraldehyde or ethylene glycol glycidylether.

(7) A stent according to the above (1) wherein said metal substrate is plated with a radiopaque metal on at least a part thereof.

(8) A stent wherein the surface that is brought in contact with the blood is rendered antithrombogenic, and the surface that is not brought in contact with the blood is rendered radiopaque.

DETAILED DESCRIPTION OF THE INVENTION

The stent of the present invention comprises a substrate of any desired material such as a resin or a metal.

Preferably, the material used for the stent substrate is a biocompatible material such as stainless steel, tantalum, superelastic nickel-titanium (Ni—Ti) alloy, or a thermoplastic polymer.

The stent of the present invention is not limited for its shape, however preferably it is expandable in radial direction from the constricted state to the expanded state, and flexible in axial direction.

Figure 1A:
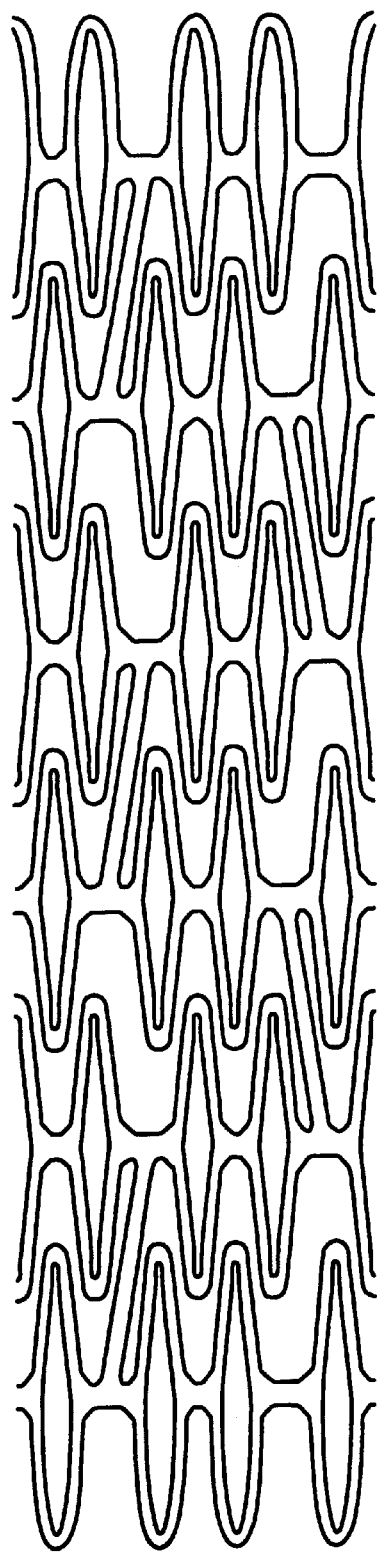
FIGS. 1(a) and (b) are foldout views of an embodiment of the stent according to the present invention.
Figure 1B:
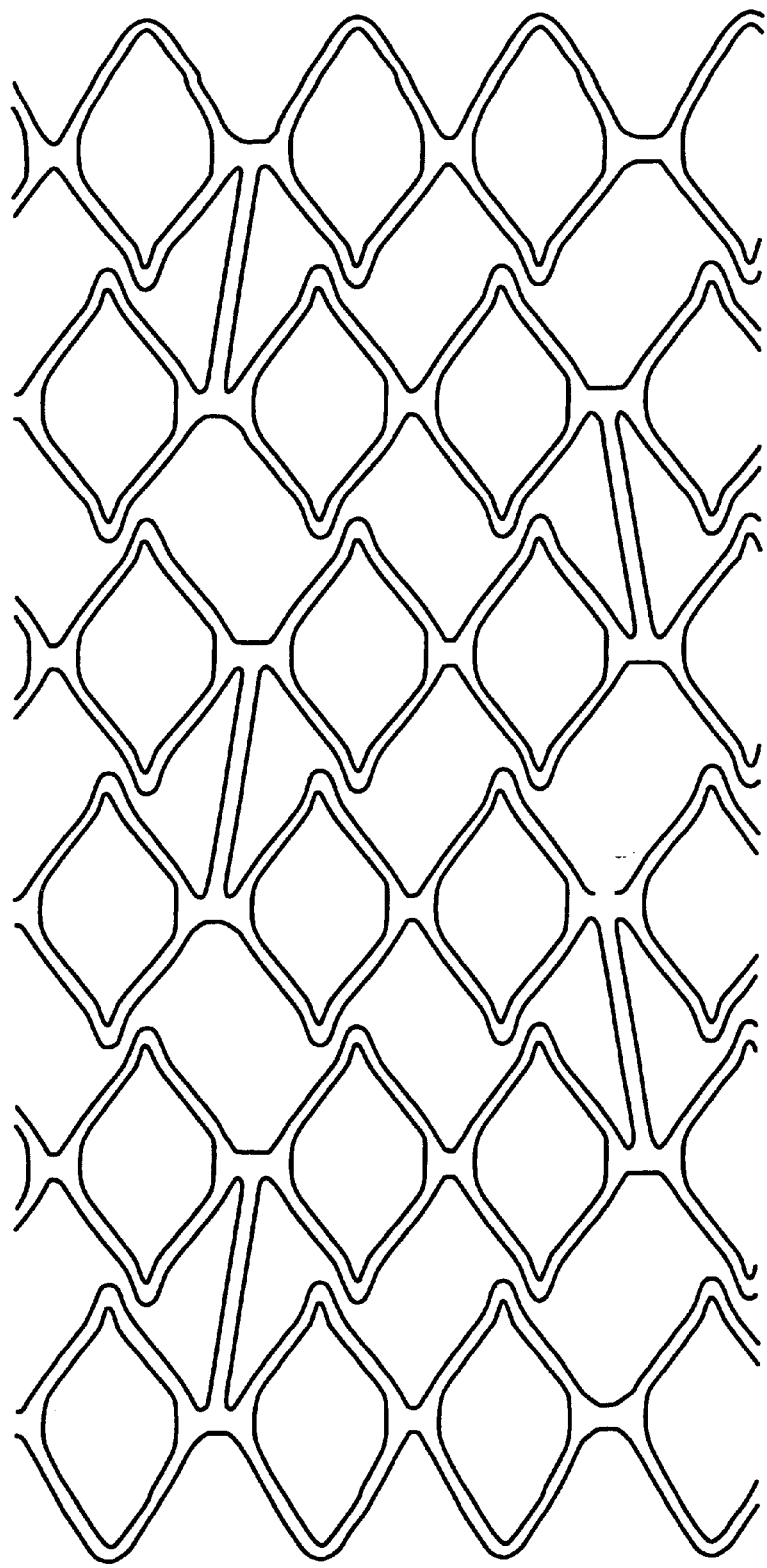

The stent may typically have a cylindrical shape in the form of a coil, net, or bellows, and the stent may comprise either a single unit or a train of two or more units. FIG. 1 is an embodiment of the stent in its constricted state. (a) is a foldout view of the constricted state, and (b) is a foldout view of the expanded state.

Figure 2:
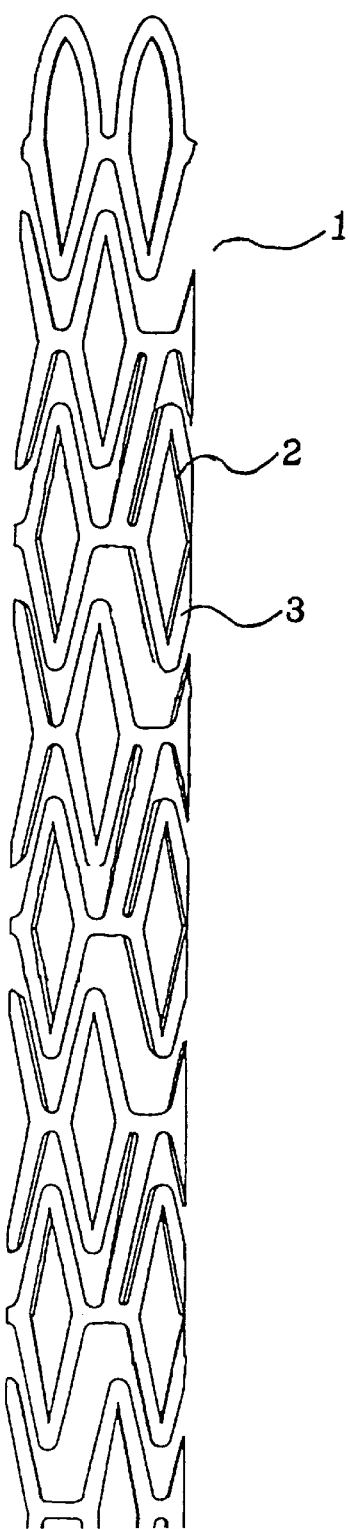
FIG. 2 is a perspective view of an embodiment of the stent according to the present invention
Figure 3:
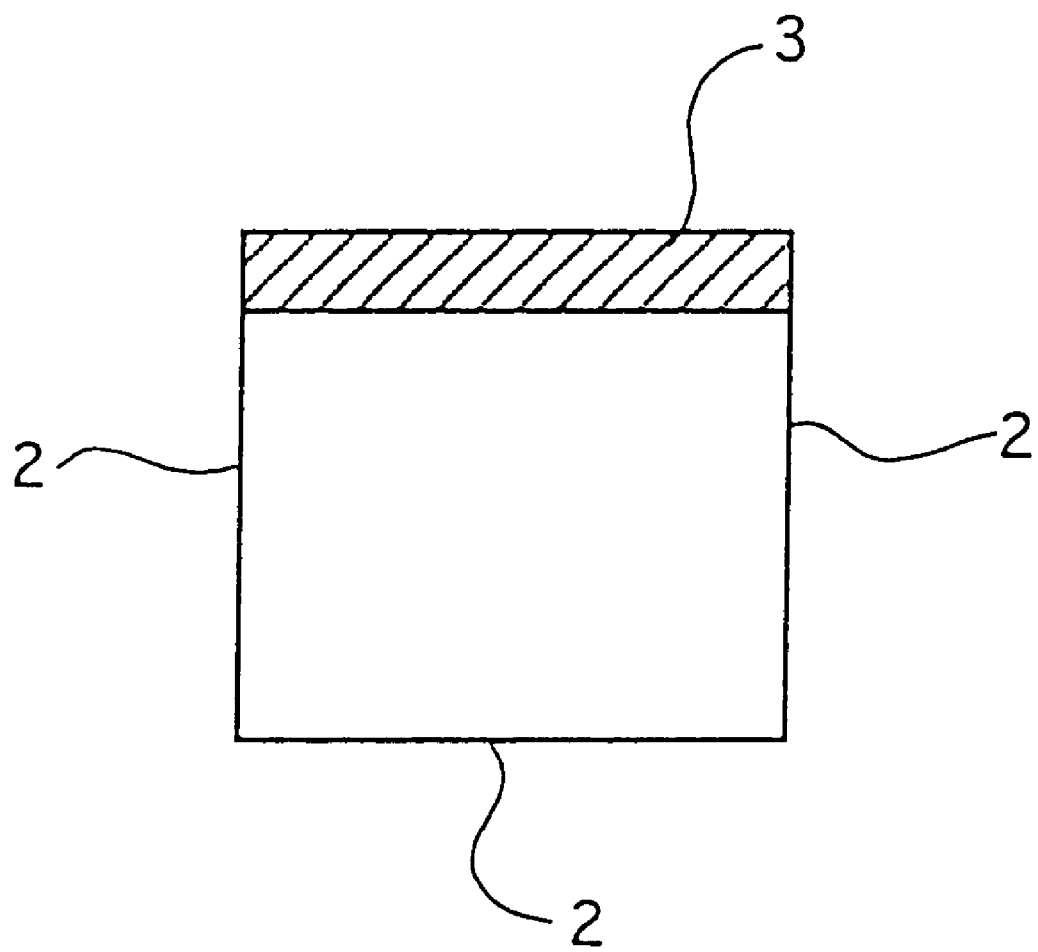
FIG. 3 is a cross-sectional view showing one unit of the stent of FIG. 2.

A perspective view of the exemplary stent of the present invention is shown in FIG. 2. The stent 1 of the present invention has an antithrombogenic agent 2 covalently bonded thereto, and a radiopaque metal plated layer 3 deposited on at least a part of the stent. In the embodiment shown in FIG. 2 whose part is cross-sectionally shown in FIG. 3, the antithrombogenic agent 2 is covalently bonded to the surface of the stent that becomes in contact with the blood, and the radiopaque metal plated layer 3 is deposited on the stent surface that will not be in contact with the blood. in other word, the outer surface of the stent is deposited a metal plated layer 3, and the backside and the flank of the outer surface of the stent are covalently bonded with the antithrombogenic agent 2.

The surface of the stent is surface treated to impart either antithrombogenicity or X-ray opacity. The stent surface may be treated by either or both of such surface treatments. When treated by both surface treatments, the surface is preferably rendered radiopaque first, and then, antithrombogenic.

Exemplary radiopacity treatments include plating of a radiopaque metal such as gold, argent, platinum, iridium, tantalum and the like on the stent surface. It has been thus far considered difficult to effect any further surface treatment on the radiopaque metal-plated surface since many radiopaque metals are noble metals and the radiopaque metal-plated surface is inactive, and no attempt has been made to render the metal-plated surface thromboresistant. It is the present invention that has for the first time enabled to provide a stent having both the radiopacity and antithrombogenicity by a convenient process, namely, by metal plating the stent on desired surface, and subsequently effecting the antithrombogenic treatment on another desired surface. The stent is preferably metal-plated on its outer surface or a part thereof that will not be in contact with the blood. In view of X-ray opacity, the stent is preferably plated along its full length to enable satisfactory visibility. The preferable radiopaque metal is gold in view of its excellent stability. Each metal has inherent radiopacity, and therefore, the metal should be plated to a thickness that would enable angiography after the stent placement. In the case of gold, the radiopaque layer is preferably plated to a thickness of from 10 to 40 $\mu$m.

When a stent of cylindrical shape is plated on its outer surface, the plating should be conducted after masking the inner surface to avoid the metal deposition thereto. Preferably, a metal cylinder pipe is rendered bunged at both ends to be sealed not to enter inside the plating liquid. Subsequently the sealed cylinder pipe is metal-plated, and then the cylinder pipe is given a shape of a stent by stamping or treating with laser.

Irrespective of whether or not the stent is rendered radiopaque as describe above, the stent is rendered antithrombogenic as described below.

(1) The surface of the stent is first treated with an oxidizing agent.

Exemplary oxidizing agents are halogen gas, chromic acid derivatives and the like, but ozone is more preferred. A treatment with ozone is one of the most strong oxidization treatment, and therefore, adequate for activating chemically inactive surface of a metal such as stainless steel.

In the course of oxidation by ozone, the substrate surface is not only chemically activated but also physically activated to result in surface roughening. The minute surface irregularities formed will serve an anchor for the coupling agent used in the heparin immobilization. The impurities on the surface which may interfere with the anchoring of the coupling agent are also decomposed through the oxidation by the ozone treatment, enabling a strong heparin immobilization.

The ozone is produced in an ozone generator by oxidation of oxygen, and the ozone treatment is effected by bringing the thus generated ozone in contact with the stent. The ozone treatment is carried out at an ozone concentration, oxygen (ozone) flow rate, reaction temperature and reaction period adequately selected according to the material of the stent treated. When the surface treated is a metal surface, the ozone treatment may be carried out under severer conditions than the case of treating an organic resin surface.

The ozone concentration is preferably in the range of from 20 to 100 mg/l. The ozone concentration of less than 20 mg/l will result in an insufficient surface activation while the ozone concentration of more than 100 mg/l may involve some risk of non-uniform reaction.

The oxygen (ozone) flow rate is preferably in the range of from 50 to 1,000 ml/min. The flow rate of less than 50 ml/min may result in localized reaction, and the flow rate of more than 1,000 ml/min is uneconomical since some of the ozone will not be involved in the surface activation.

The reaction temperature may be determined by raising the temperature within the range of 0 to 70° C. according to a character of the material if the stent surface is non-oxidizable at normal temperature.

The reaction period is preferably within the range of from 30 to 120 minutes. The reaction will be difficult to control if the ozone treatment were carried out within 30 minutes. The reaction period of longer than 120 minutes is too long and inefficient.

(2) Next, an antithrombogenic agent is covalently bonded to the stent surface through a coupling agent having two or more amino groups and a crosslinking agent having two or more aldehyde groups or epoxy groups.

The activated surface is reacted with a coupling agent having two or more amino groups which temporarily enable ionic bonding of the antithrombogenic molecule (preferably, heparin molecule) to the activated surface. Exemplary coupling agents include polyethylene imine, polyethylene glycol diamine, ethylenediamine, and tetramethylenediamine.

The heparin molecule is brought in contact with the substrate surface having the thus attached amino groups to jonically bond the heparin to the substrate. The heparin is temporarily attached to the substrate surface for covalent bonding in the subsequent step.

The heparin molecule that is brought in contact with the substrate surface may be the heparin molecule itself. The heparin molecule, however, is preferably the one having a part of its N-sulfate group moieties desulfated and converted to primary amine moieties. The percentage of the primary amino group in the heparin molecule, however, may be preferably adjusted to the range of from 5 to 25% since heparin is inactivated in proportion to the degree of such desulfation. When heparin or aminated heparin is used for the antithrombogenic agent, the stent will retain sufficient antithrombogenicity for about two weeks after the stent placement in the lesion. Use of the heparin or the aminated heparin also results in high restoration of the body tissue.

The antithrombogenic agent may alternatively comprise a compound which is antithrombogenic and capable of suppressing smooth muscle cell migration such as a calcium antagonist, an inhibitor for angiotensin-converting enzyme, or an antagonist for the receptor of platelet membrane glycoprotein (IIb–IIIa antagonist). The antithrombogenic agent should also be capable of ionically binding to the amino group.

a) The coupling agent may be attached to the substrate surface by applying the solution of the coupling agent to the substrate surface through coating or dipping. The solution may be adjusted to a pH of from 4 to 12 since the pH outside this range may result in the outflow of the ion in some substrate metal material to result in the loss of activated surface. The reaction temperature is preferably in the range of from 0° C. to less than 80° C. The reaction temperature of lower than 0° C. results in reduced reactivity, while the reaction temperature above 80° C. is associated with the risk of denaturation of the coupling agent. The reaction period is preferably from 10 minutes to 24 hours. The reaction period of less than 10 minutes results in insufficient reaction, while the reaction period of more than 24 hours is associated with the risk of denaturation of the coupling agent at some pH or temperature.

Next, the antithrombogenic agent, preferably heparin, is ionically bonded to the substrate by means of applying the heparin solution to the substrate surface having the coupling agent attached thereto through coating or dipping. The solution applied is preferably adjusted to a pH of from 2 to 5 since the pH of less than 2 results in a reduced heparin stability while the pH in excess of 5 results in the reduction of the positive charge on the substrate surface, leading to a reduced amount of the heparin bonded. The reaction temperature is preferably in the range of from 0 to 80° C. since the reaction temperature of lower than 0° C. results in a significantly reduced ionic bonding rate of the heparin while the reaction temperature of higher than 80° C. results in a reduced heparin stability. The reaction period is preferably from 10 minutes to 24 hours since the reaction period of less than 10 minutes results in an insufficient ionic bonding while the reaction period of more than 24 hours results in a reduced heparin activity. The heparin concentration is preferably 0.05% or more and the saturation concentration or less.

b) Next, a compound having at least two aldehyde or epoxy groups is reacted as a crosslinking agent between the coupling agent and the heparin molecule in order to covalently bond the antithrombogenic agent, preferably heparin, to the substrate surface. Exemplary crosslinking agents are glutaraldehyde and ethylene glycol diglycidylether. When a dialdehyde derivative is used for the crosslinking agent, the covalent bond formed is unstable, and a subsequent stabilization by reduction is required.

The formation of covalent bond by crosslinking agent may be effected by applying a solution of the crosslinking agent to the substrate surface through coating or dipping. The solution of the crosslinking agent preferably has a concentration in the range of from 0.1 to 0.5%, since the concentration of less than 0.1% results.in an insufficient crosslinking and the concentration higher than 0.5% adversely affects the heparin activity. The pH is preferably in the range of from 2 to 5 since a pH of less than 2 results in a reduced heparin stability, and a pH higher than 5 results in the rapid release of the ionically bonded heparin from the substrate before the crosslinking. The reaction temperature is preferably in the range of from 0 to 60° C. since the reaction temperature lower than 0° C. results in an insufficient reaction and the reaction temperature higher than 60° C. will induce heparin inactivation. The reaction period is preferably in the range of from 30 minutes to 24 hours since the reaction period shorter than 30 minutes is insufficient for completion of the crosslinking and the reaction period longer than 24 hours will induce heparin inactivation.

When a dialdehyde derivative is used for the crosslinking agent, the covalent bond formed is unstable as mentioned above. The unstable bond formed (Schiff base) is subsequently stabilized by applying a solution of a reducing agent through coating or dipping. In a preferred embodiment, the reducing agent is added to the solution which is undergoing the crosslinking reaction, and then, the heparin immobilization can be completed as a reaction within the reaction cascade and the reduction can be completed with no breakage of the unstable covalent bond. The reducing agent in an amount at least stoichiometric with the bond to be reduced is used for the reduction. Addition of the reducing agent of smaller amount at a higher concentration is desirable for avoiding the change in reaction conditions such as the temperature and the concentration of the crosslinking agent. The reaction period should be limited to no more than 2 hours to thereby avoid the heparin inactivation.

The present invention is described in further detail by referring to Examples and Comparative Examples, which by no means limit the scope of the invention.

EXAMPLES

Example 1

A stainless steel plate (material: SUS 316L) of 1 mm thick was cut into samples of 8 mm×8 mm. The sample plates were treated with ozone at an ozone concentration of 88 mg/l and an oxygen flow rate of 800 ml/min for reaction period of 0, 30, 60, 120 and 180 minutes. The sample plates were evaluated for their surface elementary oxygen percentage by electron spectroscopy for chemical analysis (hereinafter abbreviated as ESCA). The results are shown in Table 1.

TABLE 1

Percentage of elementary oxygen on ozone-treated samples

| Ozone reaction period, min. | 0 | 30 | 60 | 120 | 180 |
|---|---|---|---|---|---|
| Percentage of elementary oxygen | 40.49 | 51.12 | 60.29 | 61.90 | 60.92 |

The percentage of elementary oxygen becomes substantially constant at a reaction period of 60 minutes, and it was likely that the oxide on the sample surface had become saturated at the reaction period of 60 minutes. Therefore, the reaction period of 60 minutes or more would be unnecessary while the reaction period of less than 60 minutes would result in an insufficient reaction since the percentage of the oxide on the stent surface is still increasing. By measuring the percentage of elementary oxygen as described above, it has been possible to confirm that the substrate surface is activated by ozone treatment and to determine the optimal conditions for the ozone treatment of the SUS 316L. Optimal conditions can be determined for other metal substrate materials in a similar manner.

Example 2

The sample plates of Example 1 were immersed in 0.5% aqueous solution of polyethylene imine (hereinafter abbreviated as PEI) for 5 hours to immobilize PEI on the sample surface. The samples were evaluated by abrasion test by rubbing the sample surface with a polyethylene terephthalate film and analyzing each sample by ESCA to thereby confirm that the PEI is not only present in an unbound state, but bonded to the sample surface. The element measured in ESCA was nitrogen from PEI. The results are shown in Table 2.

TABLE 2

Percentage of elementary nitrogen on each sample surface

| Ozone reaction period, min. | 0 | 30 | 60 | 120 | 180 |
|---|---|---|---|---|---|
| Before the abrasion test | 11.43 | 15.76 | 17.14 | 14.27 | 12.10 |
| After the abrasion test | 4.87 | 10.75 | 12.62 | 10.63 | 11.04 |

Removal of the PEI was clear in the non-ozone treated sample (the sample with the ozone reaction period of 0 minute), and it was confirmed that maximum amount of PEI is immobilized when the sample plates are ozone-treated for a reaction period of 60 minutes. As described above, the substrate surface is effectively activated by the ozone treatment, and the optimal conditions determined in Example 1 for SUS 316L are effective for the immobilization of PEI.

Example 3

In order to jonically bond the heparin to the sample substrate, a solution of heparin having a part of its N-sulfate group moieties desulfated and converted to primary amine moieties (synthesis of the aminated heparin was conducted in accordance with JP-B-8-38851) was prepared by dissolving the aminated heparin in 50 mM succinate buffer, pH 4.0 to a concentration of 0.05%, and the sample substrates of Example 2 which have been ozone-treated for 60 minutes were immersed in the solution at 45° C. for 2 hours. The samples of this stage (in which heparin is attached to the substrate through ion bond) are designated samples A.

All of the samples A (except for the samples which are not subjected to further treatments) were subjected to a series of treatments as described below to attach the heparin to the substrate through a covalent bond.

The samples A were immersed in 2 ml of 0.1%, 0.2%, 0.3% and 0.5% aqueous solutions of glutaraldehyde (which serves the crosslinking agent) at 55° C. for 2 hours, respectively. After the immersion, 0.2 ml of aqueous solution of sodium cyanoboron hydride at a concentration 20 times higher than the glutaraldehyde solution was added to each glutaraldehyde solution, and the solution was thoroughly stirred and allowed to stand at 55° C. for 2 hours to reduce the bonding sites. The samples were then immersed in distilled water at 55° C. for 1 hour to remove the excessive crosslinking agent and the reducing agent. The resulting samples were designated samples B1, B2, B3 and B5 samples.

The above-described procedure was repeated except that the crosslinking and reducing reactions were conducted at 4° C. The samples were designated C1, C2, C3 and C5 samples.

The samples were washed by circulating physiological saline at 37° C. for 3 days at a flow rate of 410 ml/min, and the samples were evaluated for their heparin activity remaining on their surface by using a commercially available measurement kit (Test-Team Heparin s kit, Daiichi-Kagaku Yakuhin). The results are shown in Table 3.

TABLE 3

Heparin activity remaining on the sample surface [IU × $10^{-3}$/cm$^2$]

|  | A | B1 | B2 | B3 | B5 |
|---|---|---|---|---|---|
| Unwashed | 153.7 | 129.6 | 86.1 | 45.9 | 6.7 |
| 3 days | 44.2 | 81.6 | 54.2 | 27.7 | — |

|  | C1 | C2 | C3 | C5 |
|---|---|---|---|---|
| Unwashed | 151.9 | 161.0 | 160.3 | 101.6 |
| 3 days | 105.3 | 131.6 | 132.1 | — |

Effects of crosslinking for the heparin immobilization were evident from the results of the non-crosslinked sample A which underwent clear reduction in the heparin activity. Optimal crosslinking in Example 3 resulted at the temperature of 4° C. and the glutaraldehyde concentration of 0.2% or 0.3%.

Example 4

The sample C3 which exhibited the optimal results in Example 3 and the contrast sample (untreated stainless steel.sample, SUS 316L) were subjected to an ethylene oxide gas sterilization (hereinafter referred to as EOG sterilization), and then to a platelet expandability test. The sterilization was conducted under the conditions of the temperature of 50° C., humidity of 65%, EOG pressure of 0.7 kgf/cm$^2$, reaction period of 3 hours, and gas replacement of 3 times. The samples were left for 7 days after the sterilization. The results are shown in Table 5. Reactivity of the sample surface with the platelets can be determined from the results.

The procedure of the platelet expandability test and its significance are as described below.

The sample surface was brought in contact with platelet-rich plasma (hereinafter referred to as PRP) containing preliminarily adjusted number of platelets for a fixed time, and the samples were evaluated for their antithrombogenic level by the number and morphology of the platelets that became attached to the sample surface.

More illustratively, human vein blood (having 3.8% sodium citrate added thereto) was centrifuged to separate PRP (platelet-rich plasma), and a further centrifugation was conducted to obtain platelet-poor plasma (hereinafter referred to as PPP). The thus prepared PRP and PPP were used to prepare a PRP wherein the number of the platelets contained is adjusted to 10×10$^4$/μl. 200 μl of the adjusted PRP was dropped onto a 8×8 mm sample, and a polystyrene petri dish was placed on the droplet to adjust the liquid thickness to 2 mm. After leaving for 30 minutes, the sample was washed, fixed with 1% aqueous solution of glutaraldehyde, and observed and photographed with an electron microscope. The number of platelets adhered to unit area sample was counted on the electron microphotograph for each morphological category as described below. The results are shown in Table 4.

TABLE 4

Results of platelet expanding ability test [/0.03 mm$^2$]

|  | Type I | Type II | Type III |
|---|---|---|---|
| Contrast (SUS 316L) | 1 | 7 | 37 |
| Heparin coated sample (C3) | 13 | 7 | 0 |

Type I: The platelets underwent a change in their morphology from disk-like normal morphology to spherical morphology. Few pseudopods were observed.
Type II: Several or more pseudopods were observed. The cells started to expand.
Type III: the cells fully expanded and collapsed.

Surface reactivity of the stainless steel substrate to the platelets was reduced by the heparin coating to result in the antithrombogenicity of the substrate.

Example 5 and Comparative Examples 1 and 2

Nine stainless steel pipes (material: SUS 316L; length: 20 mm; outer diameter: 1.4 mm; wall thickness: 0.1 mm) were laser-worked into balloon-expandable stents. Of these stent samples, 3 stent samples were coated with heparin under the conditions of Example 3, sample C3 (hereinafter referred to as HC (heparin-coated) samples); and 3 stents samples were coated by conventional technique, namely, with heparin-benzalkonium (heparin-dimethylstearylbenzyl chloride) for contrast purpose (hereinafter referred to as HB (heparin-benzalkonium samples). The remaining 3 stent samples were use with no further treatment (hereinafter referred to as NH (non-heparin) samples).

The stents were washed by circulating physiological saline at 37° C. for 14 days at a flow rate of 410 ml/min. The stents were evaluated for their heparin activity by repeating the procedure of Example 3. The results are shown in Table 5.

TABLE 5

Heparin activity after washing [IU × $10^{-3}$/cm$^2$] (n = 3)

| Sample | HC | HB | NH |
|---|---|---|---|
| Activity | 49.3 | 0.3 | 0 |

The results demonstrate that the activity can be retained for a prolonged period by heparinizing the substrate surface in accordance with the method of the present invention.

Example 6 and Comparative Examples 3 and 4

The procedure of Example 5 and Comparative Examples 1 and 2 was repeated to prepare 3 types of stents (3 stents/type). The resulting 9 stents were sterilized by EOG sterilization under the conditions of Example 4, and the stents were allowed to stand for 7 days to remove the EOG. The stent was then inserted in abdominal aorta (blood vessel diameter, 3 mm) of 9 white rabbits (Kitayama-Rabeth) having weights of 2.5 to 3.0 kg from their femoral artery by using a balloon catheter, and the catheter was placed in the abdominal aorta after the expansion. The balloon used had an inflated diameter of 3 mm. An anticoagulation treatment by heparin administration was conducted during the operation. Two weeks after the operation, the animals were administered with heparin, and sacrificed by excessive administration of anesthetic to remove the stent. Little or no thrombus adhesion was found in the case of three stents of HC samples. On the other hand, in the HB and NH stent samples, a large amount of thrombus (about to induce stenosis) was observed in ⅔ stents, and thrombus adhesion of moderate degree was found on the remaining ⅓ stent.

The blood vessel within which the stent had been placed was embedded in paraffin to prepare a soft tissue pathological specimen, and the specimen was examined for hemangioendothelial cells. No neoblastic smooth muscle tissue was found in the cases of the HC and HB stent samples while neoblastic sign was noticed in one case of the NH stent samples. The results are shown in Table 6.

TABLE 6

Results of animal experiment (n = 3)

| Sample | HC | HB | NH |
|---|---|---|---|
| Thrombus | ⊚ | X | X |
| New tissue | ⊚ | ⊚ | Δ |

⊚: thrombus or neoblastic sign was noticed in 0/3 cases.
Δ: thrombus or neoblastic sign was noticed in 1/3 cases.
X: thrombus or neoblastic sign was found in all 3 cases.

Example 7

Of 2 stainless steel pipes (material: SUS 316L; length: 20 mm; outer diameter: 1.4 mm; wall thickness: 0.1 mm), one pipe was electroplated on its outer surface with gold to a thickness of 30 $\mu$m. The stainless pipes were laser-worked into balloon-expandable stents, and the stents were coated with heparin under the conditions of Example 3, sample C3. The stent was then expanded with a balloon to evaluate visibility by radiography. The gold-plated stent was radiographically visible not only to its outer contour but also to its laser-cut design while the non-plated stent was substantially radiotranslucent.

In the foregoing Examples, the stent of the present invention has been described by featuring the case of a stainless steel stents. It should be noted, however, that the antithrombogenic treatment of the present invention may be effected on a balloon-expanded stent. which has been plated with gold on entire surface, or an expandable stent which has been coated with an appropriate synthetic resin (see JP-B-6-38851 for the type of resins that can be used for such coating) after an optional radiopacity treatment.

The antithrombogenic and/or radiopaque treatment of the present invention may be carried out not only on stents, but also on various metal medical materials and equipment which are brought in contact with blood.

BENEFITS OF THE INVENTION

As described above, the stent of the present invention having an antithrombogenic agent immobilized on its surface has realized a strong bond between the heparin molecule and the substrate surface which is superior to the conventional coating of heparin-benzalkonium, and therefore, the antithrombogenic activity is maintained under the severe conditions of blood flow. As a consequence, use of the stent of the present invention will avoid restenosis due to adhesion of the thrombus of the lesion after the stent placement, and alleviate the clinical treatment such as administration of the antithrombotic agent.

The immobilization of the antithrombogenic agent also reduces the event of restenosis through vascular thickening induced by vascular smooth muscle cell migration and proliferation.

In addition, the substantially radiotranslucent stent can be simultaneously rendered antithrombogenic and radiopaque in a simple manner by plating a radiopaque metal on the stent before the immobilization of the antithrombogenic agent on the stent surface.

We claim:

1. A radiopaque, antithrombogenic stent suitable for insertion in the bloodstream, comprising a cylindrical metal substrate having an outer surface, wherein a radiopaque metal layer is formed on said outer surface, and wherein said cylindrical metal substrate is formed in the shape of a stent by stamping or by laser treatment, and said substrate is made antithrombogenic by treating the metal substrate with an oxidizing agent and covalently bonding an antithrombogenic agent to the metal substrate through a coupling agent having at least two amino groups and a cross-linking agent having at least one group selected from the group consisting of two aldehyde and epoxy groups.

2. A radiopaque, antithrombogenic stent according to claim 1, wherein said oxidizing agent is ozone.

3. A radiopaque, antithrombogenic stent according to claim 1, wherein said antithrombogenic agent is aminated heparin.

4. A radiopaque, antithrombogenic stent according to claim 1, wherein said metal substrate comprises stainless steel.

5. The radiopaque, antithrombogenic stent according to claim 1, wherein said coupling agent is at least one member selected from the group consisting of polyethylene imine, polyethylene glycol, diamine, ethylenediamine and tetramethylenediamine.

6. A radiopaque, antithrombogenic stent according to claim 1, wherein said cross-linking agent is glutaraldehyde or ethylene glycol glycidyl ether.

7. A radiopaque, antithrombogenic stent according to claim 1, wherein said stent shape is selected from coil shape, net shape, and bellow shape.

8. A radiopaque, antithrombogenic stent of claim 1, wherein said radiopaque layer is selected from the group consisting of gold, silver, platinum, iridium and titanium.

9. A radiopaque, antithrombogenic stent according to claim 8, wherein said radiopaque layer comprises gold.

10. A radiopaque, antithrombogenic stent suitable for insertion in the bloodstream, comprising a cylindrical metal substrate having an outer surface, wherein a radiopaque metal layer is formed on at least a portion of said outer surface, and the surface of said cylindrical metal substrate other than the portion having said radiopaque layer formed thereon is rendered antithrombogenic by treating the metal substrate with an oxidizing agent, and covalently bonding an antithrombogenic agent to the metal substrate through a coupling agent having at least two amino groups and a cross-linking agent having at least two aldehyde and/or epoxy groups.

* * * * *

UNITED STATES PATENT AND TRADEMARK OFFICE
CERTIFICATE OF CORRECTION

PATENT NO. : 6,174,326 B1
DATED : January 16, 2001
INVENTOR(S) : T. Kitaoka et al.

It is certified that error appears in the above-identified patent and that said Letters Patent is hereby corrected as shown below:

Column 1,
Line 27, delete "a n" and insert -- an --.

Column 2,
Line 53, delete "bonde d" and insert -- bonded --.

Column 3,
Line 13, delete b lood" and insert -- blood --.

Column 8,
Line 33, delete "jonically" and insert -- ionically --.

Column 12,
Line 15, before "said" insert -- the inner and/or side surface of --.

Signed and Sealed this

Fifteenth Day of January, 2002

Attest:

Attesting Officer

JAMES E. ROGAN
Director of the United States Patent and Trademark Office